United States Patent [19]

Rissi

[11] 4,060,731
[45] Nov. 29, 1977

[54] DENTAL X-RAY APPARATUS

[75] Inventor: Walter Rissi, Lanzenhausern, Switzerland

[73] Assignee: Gesellschaft fur Elektronische Rohren Comet Bern, Bern, Switzerland

[21] Appl. No.: 729,514

[22] Filed: Oct. 4, 1976

[30] Foreign Application Priority Data

Oct. 6, 1975 Switzerland .................. 12956/75

[51] Int. Cl.² ............................................. H05G 1/10
[52] U.S. Cl. ................................. 250/402; 250/421; 250/493; 250/439 P
[58] Field of Search ............... 250/401, 402, 421, 422, 250/493, 439 P, 523; 313/55, 57

[56] References Cited

U.S. PATENT DOCUMENTS 1,881,448  10/1932  Forde ............................ 250/439 P
3,906,235  9/1975  Fischer .......................... 250/439 P Primary Examiner—Craig E. Church
Attorney, Agent, or Firm—Townsend and Townsend

[57] ABSTRACT

Apparatus for obtaining extra- and/or intra-oral dental X-ray photographs comprising an X-ray tube having an anticathode with a plane target surface inclined with respect to the cathode-ray axis. The anticathode is disposed in a small tube within an X-ray-permeable protective sleeve. For changing the mode of operation from extra-oral to intra-oral, an adapter is fitted over the protective sleeve and actuates a change-over switch disposed within the housing of the X-ray tube. Regulating means control the intensity of the cathode-ray depending upon the position of the change-over switch for making either extra- or intra-oral photographs.

6 Claims, 7 Drawing Figures

DENTAL X-RAY APPARATUS

This invention relates to apparatus for obtaining extra- and/or intra-oral dental X-ray photographs, of the type wherein a high-voltage transformer and part of an X-ray tube are disposed in an inner casing contained with an outer housing, from an end face of which there projects an anode tube of the X-ray tube containing an anticathode and surrounded by an X-ray-permeable protective sleeve.

Dental X-ray apparatus has already been proposed with which it is possible to obtain both the conventional single photographs of teeth and panoramic photographs. Such apparatus is described, for example, in German Disclosed Application No. 2,030,624 and comprises an X-ray tube having two systems. One system includes a conical anticathode disposed in an anode tube. The other system includes a normal anticathode having a surface inclined with respect to the cathode stream. Disposed on the tube-supporting housing is a sliding screen which can be pushed back over the housing for obtaining panoramic photographs, so that the anode tube containing the conical anticathode can be inserted into the oral cavity of the person to be examined. For obtaining intra-oral photographs, the screen is pulled forward so that the anode tube is shielded. In this position, the screen exposes a window behind which the plane anticathode of the other system is situated. With this system, photographs of individual teeth or groups of teeth can be obtained. Instead of one X-ray tube having two systems, it has also already been proposed to accommodate two different X-ray tubes in one housing, a single high-voltage source being used to operate one or the other tube. The switch-over of the common high-voltage source from one system to the other is not very simple, however.

When taking panoramic photographs, it is absolutely necessary that the cathode-ray be focused with extreme accuracy on the tip of the conical anticathode.

Furthermore, it has already been proposed (cf. Swiss Pat. No. 355,225) to center the cathode-ray on the tip of the conical anticathode automatically by means of a control device. For this purpose, it is necessary to dispose within the anode tube additional test electrodes which transmit input signals for the control device as a function of the intensity of the secondary electronic radiation emitted by the anticathode. These test electrodes take up additional space in the anode tube, making the latter relatively thick. It is desirable, however, to keep the anode tube as thin as possible because the person whose dental condition is to be examined should not have to open his mouth too far.

It is an object of this invention to provide improved apparatus of the type initially described which is not subject to the aforementioned drawbacks, which allows both intra-oral and better extra-oral photographs to be obtained, and which is simpler in its construction and hence less expensive to produce than prior art apparatus of this type.

To this end, in the dental X-ray apparatus according to the present invention, the improvement comprises a plane anticathode target surface disposed within the anode tube and inclined with respect to the cathode-ray axis of the X-ray tube, regulating means dependent upon the operating state of the apparatus for varying the cathode-ray current and/or the size of the focal spot, an adapter designed to be fitted over the protective sleeve and secured to the end face of the outer housing for obtaining intra-oral X-ray photographs, a change-over switch disposed within the outer housing near the end face thereof and actuatable by the adapter for influencing the regulating means, and an X-ray-proof jacket forming part of the adapter and designed to fit over the protective sleeve coaxially therewith.

A preferred embodiment of the invention will now be described in detail with reference to the accompanying drawings, in which.

Figure 1:
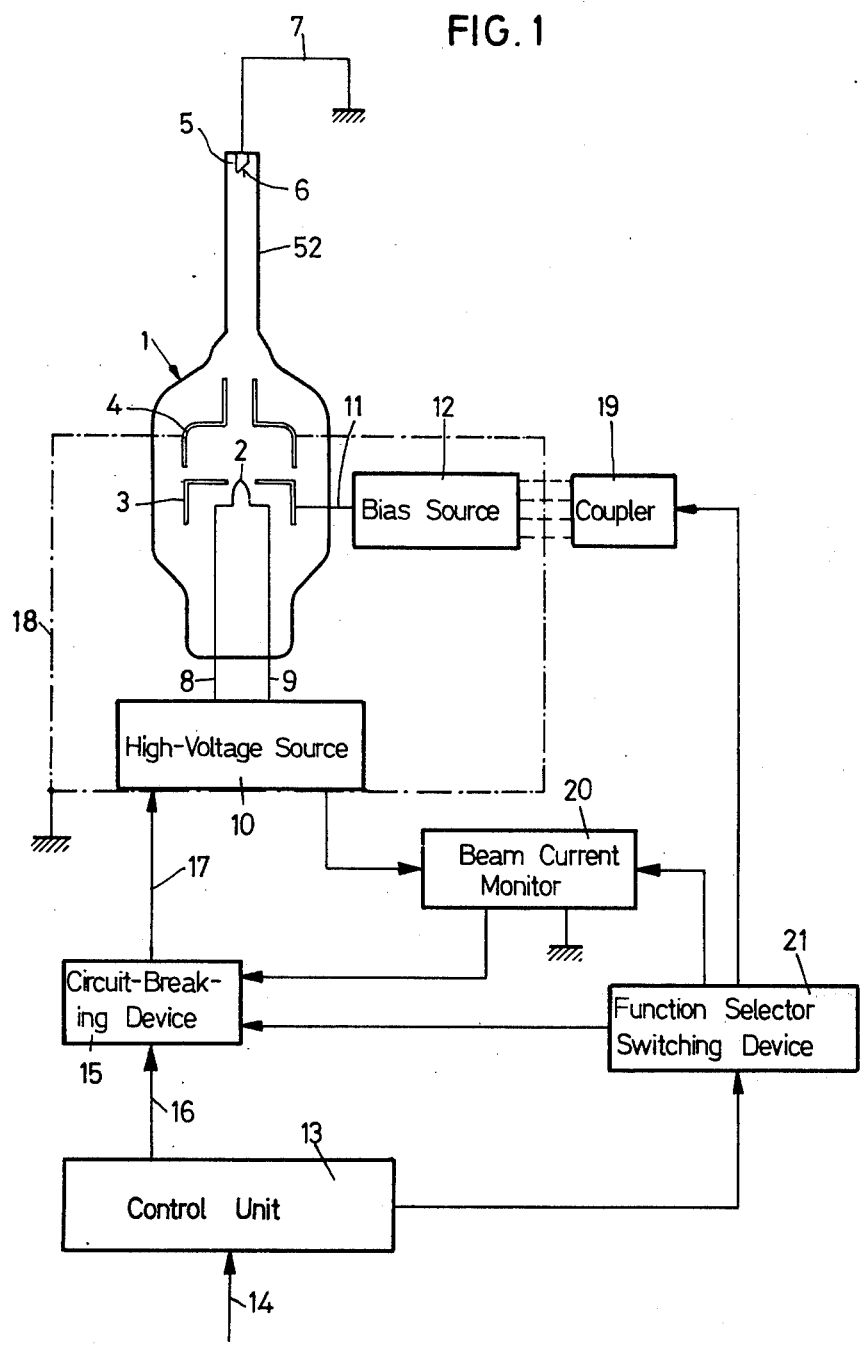
FIG. 1 is a block diagram of the apparatus.
Figure 3:
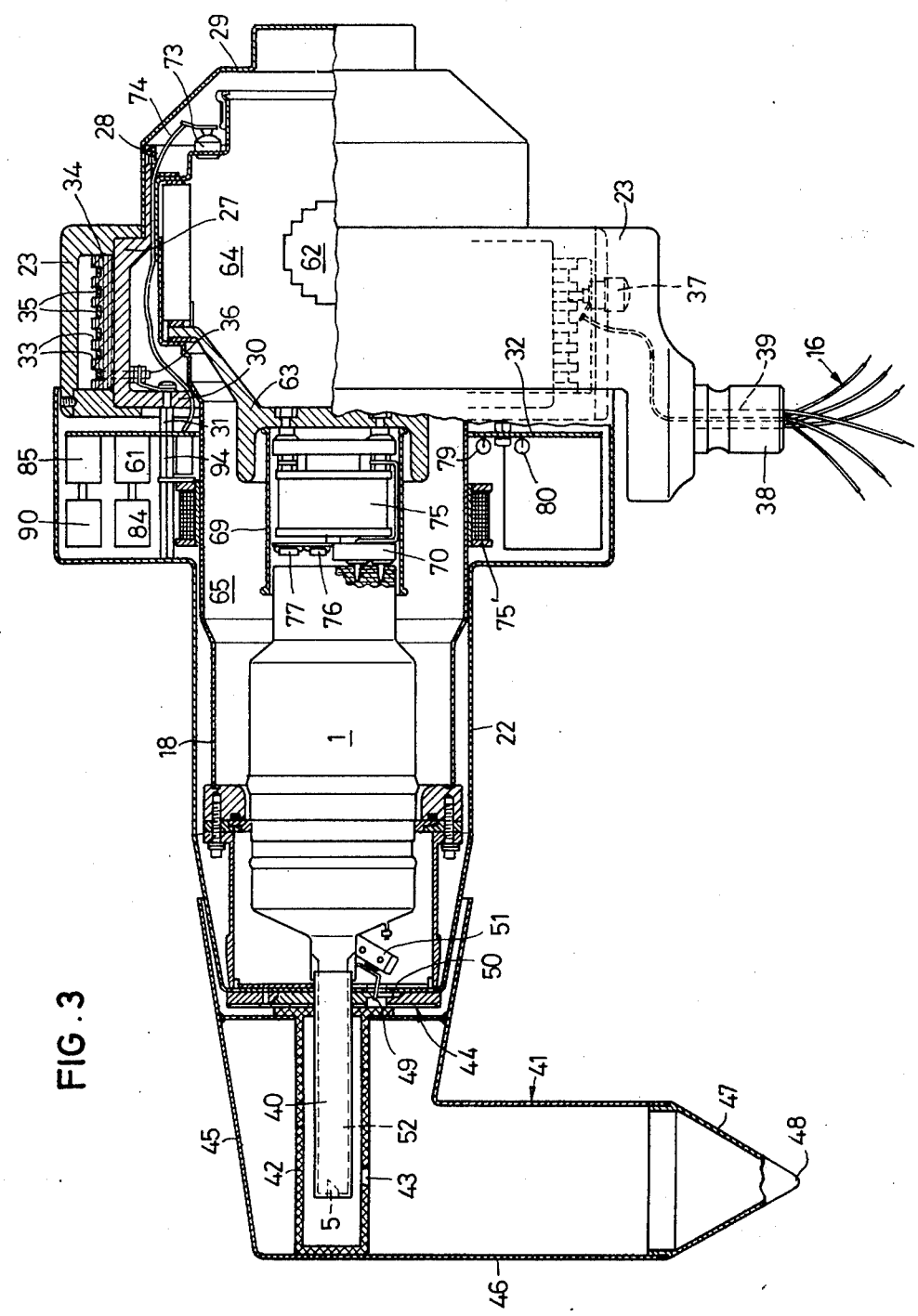
Figure 4:
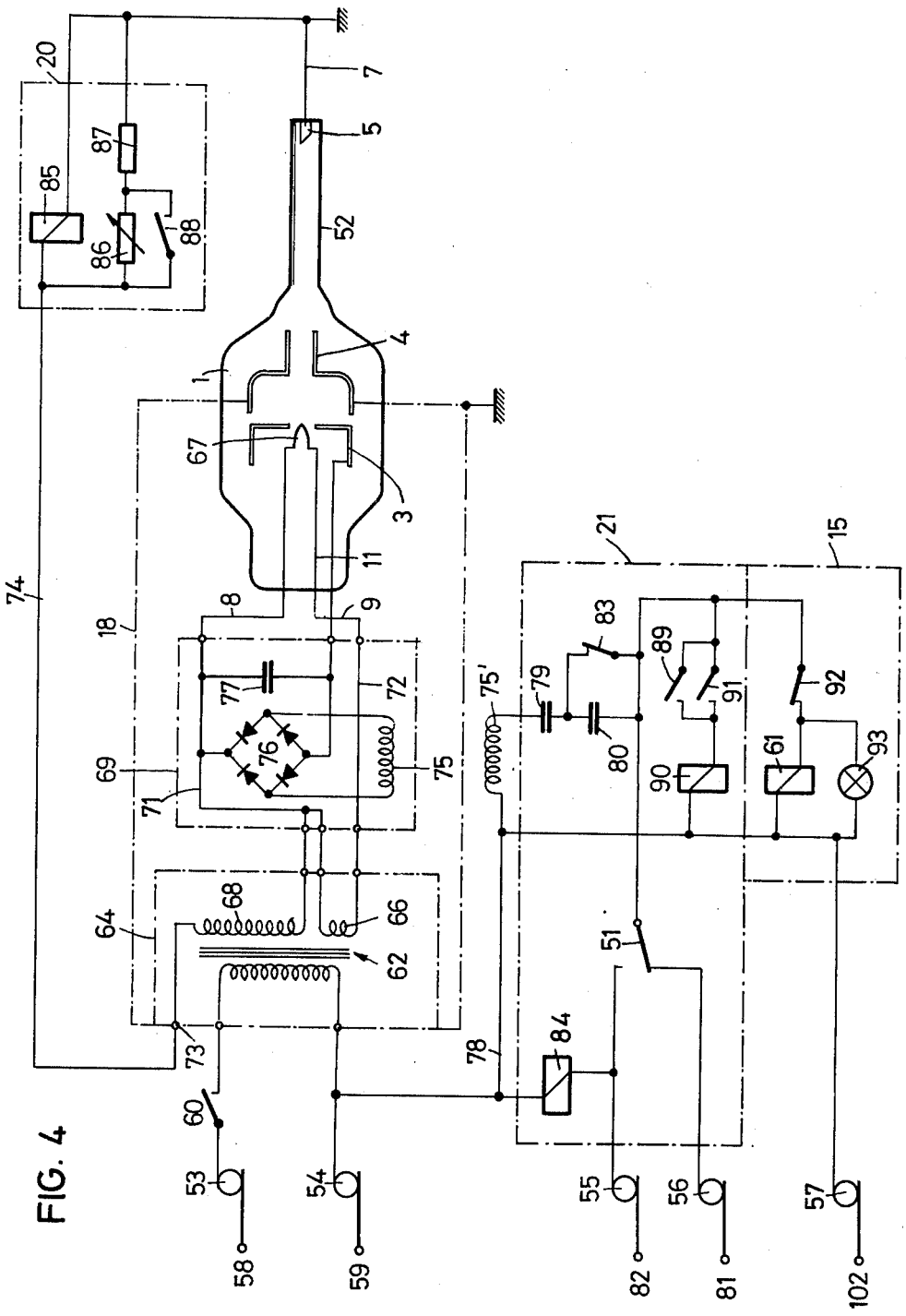
Figure 5:
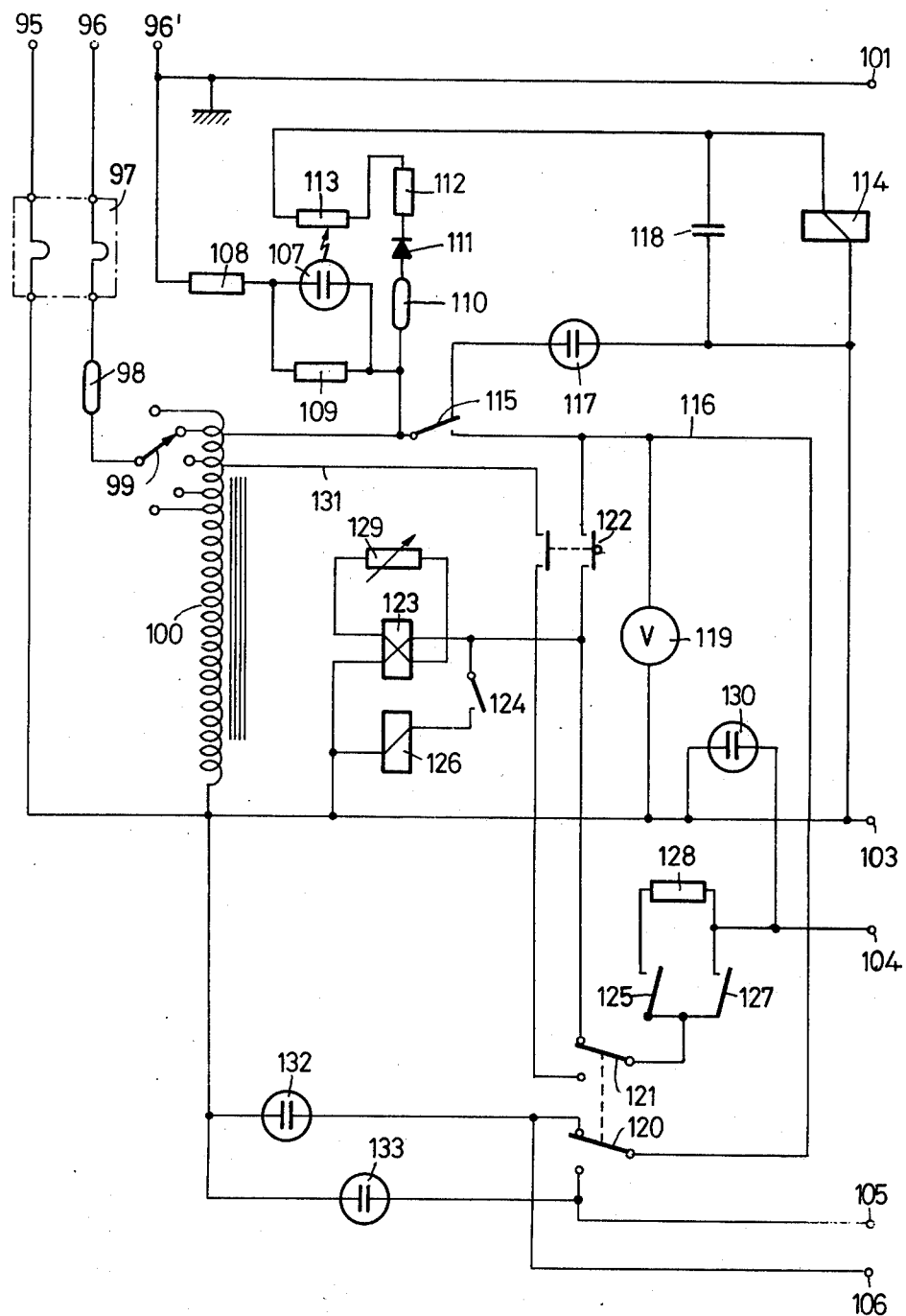
Figure 6:
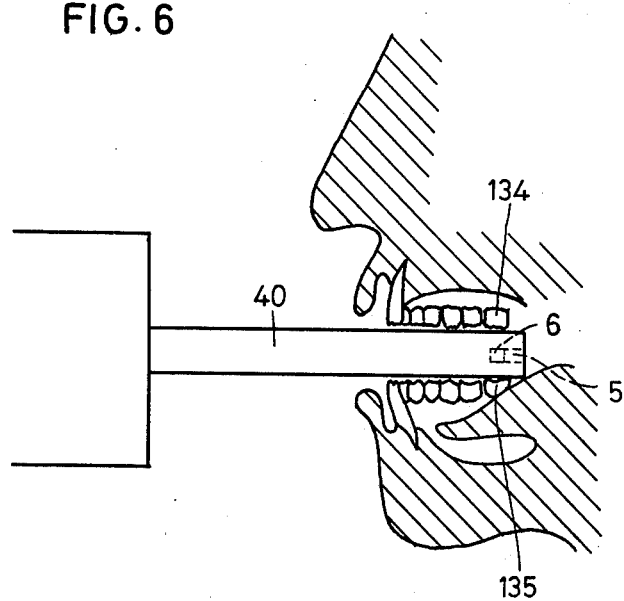
Figure 7:
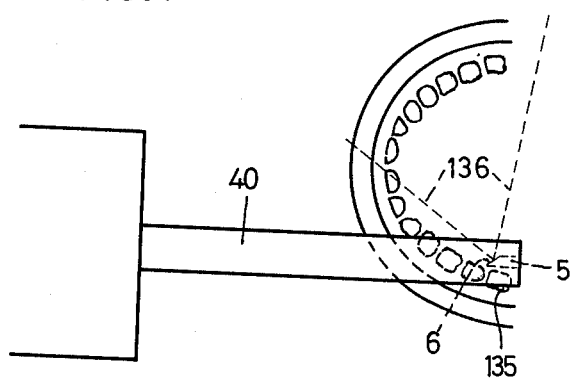

FIG. 3 is an elevation, partially in section, of a housing in which the main parts of the apparatus of FIG. 1 are accommodated, FIG. 4 is a basic diagram of the X-ray tube power supply, FIG. 5 is a circuit diagram of the control unit of the apparatus of FIG. 1, FIG. 6 is a simplified section through the oral regions of a person whose teeth are to be X-rayed, an extension of the X-ray tube being gripped between the molars, and FIG. 7 is a stylized top plan view of the lower jaw with the X-ray tube extension introduced into the oral cavity.

The apparatus illustrated by means of a block diagram in FIG. 1 comprises a single X-ray tube 1 having only one system composed essentially of a cathode 2, a modulator electrode 3, an anode 4, and an anticathode 5 disposed in an anode tube 52 and having an inclined target surface 6. The anticathode 5 is grounded via a conductor 7. The cathode 2, i.e., the filament, is connected by conductors 8 and 9 to a high-voltage source 10. The modulator electrode 3 is connected by a conductor 11 to a bias source 12.

The apparatus further comprises a control unit 13 by means of which it can be operated. The control unit 13 is connected to the mains voltage and to protective grounding by means of a three-wire cable 14. The functioning of the control unit 13 will be explained below with reference to FIG. 5. Switching orders and the power supply are conveyed to the high-voltage source 10 for the X-ray tube 1 via a contact-breaking device 15 and over multiple lines 16 and 17. The high-voltage source 10 and part of the X-ray tube 1 are accommodated in an inner casing 18. The bias source 12 is also disposed within the casing 18 and inductively supplied with the necessary energy by a coupler 19 situated outside the casing 18. A beam current monitor 20 is provided for preventing too great a cathode-ray current. A function selector switching device 21, the operation of which will be described further on, generates orders for the circuit-breaking device 15, the beam current monitor 20, and the coupler 19.

Figure 2:
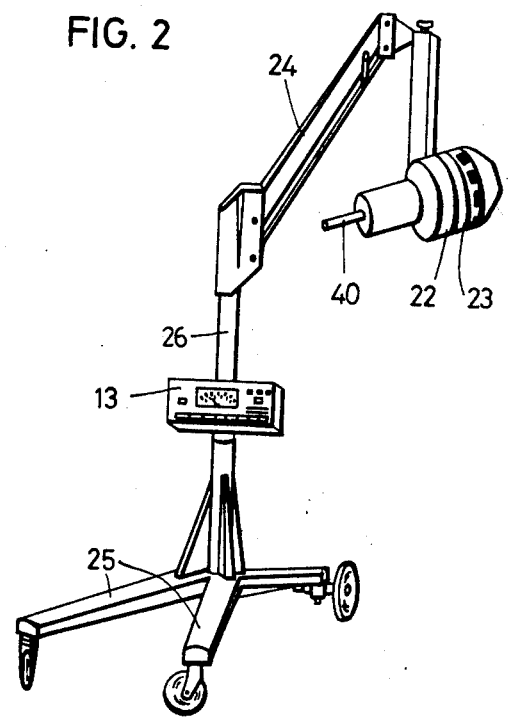
FIG. 2 is a perspective view of the apparatus of FIG. 1.

FIG. 2 shows the entire apparatus in a perspective view. It comprises an outer housing 22, enclosing the casing 18 and the major part of the X-ray tube 1, and a fastening ring 23 encircling the housing 22 and connected to a multi-jointed supporting arm 24, which is slidable along a column 26 supported at the base by legs 25. The control unit 13 is also secured to the column 26. Owing to the swivel mounting of the housing 22 in the fastening ring 23 and the supporting arm 24, the X-ray tube 1 can be adjusted and fixed in any desired position.

FIG. 3 shows the housing 22 and the parts contained therein, together with the fastening ring 23, partially in section. The housing 22 surrounds the front portion of the casing 18 and that portion of the X-ray tube 1 which is not covered by the casing 18. The fastening ring 23 surrounds an annular support member 27 to which the casing 18 is rigidly connected by means of a number of angle brackets 28, only one of which is shown. The outside opening of the annular support member 27 is closed off by a cup-shaped cover 29. Towards the inside, the support member 27 has a rim 30 projecting radially inward, to which an annular printed wiring board 32 is secured by means of bolts 31, only one of which is shown. An annular insulator 34 having six grooves 33 is pressed on over the support member 27. Disposed in each of the grooves 33 is a slip ring 35 electrically connected to a respective connecting screw 36 passing through the member 27 and electrically insulated therefrom, only one of the screws 36 being shown in FIG. 3. A carbon holder 37 is provided in the fastening ring 23 for each slip ring 35; for the sake of an uncluttered drawing, only one of the carbon holders 37 is shown. Secured to the fastening ring 23 is a gudgeon 38 for insertion into part of the supporting arm 24 in order to obtain a pivot connection. The gudgeon 38 has a bore 39 through which the multiple line 16 passes. The mains voltage and orders from the control unit 13 are supplied to the devices accommodated in the housing 22 via the multiple line 16, the carbon holders 37, the slip rings 35, and the connecting screws 36. The rotatable mounting of the support member 27 in the fastening ring 23, and the slip rings 35, enable the outer housing 22, the inner casing 18, and the X-ray tube 1 to be rotated as may be desired with respect to the fastening ring 23, without interfering with the readiness for operation.

The anode tube 52 of the X-ray tube 1, in the end of which the anticathode 5 is disposed, is surrounded by an X-ray-permeable protective sleeve 40 projecting from the end face of the housing 22. Fitted over the protective sleeve 40 is an angular adapter 41 which, for example, is not shown in FIG. 2. Within the adapter 41 is an X-ray-proof jacket 42, made preferably of lead, which coaxially surrounds the sleeve 40. An aperture 43, through which the X-rays necessary for obtaining intra-oral photographs may pass, is provided in the jacket 42. The adapter 41 may be secured to the housing 22 by means of a bayonet catch 44, for example, one part of which is disposed on the end face of the housing 22 and the other part on the adapter 41. The bayonet catch 44 is designed in such a way that the adapter 41 can be fitted to the housing 22 only in the precise position shown in FIG. 3.

The portion 45 of the adapter 41 partially surrounding the housing 22, and the angled-off portion 46 thereof, which is closed off by a tapered cover 47, are axially symmetrical and made of plastic. The portion 46, and particularly the tip 48 of the cover 47, aid the dentist who wishes to make an intra-oral photograph in correctly adjusting the distance between the X-ray source, i.e., the anticathode 5, and the object to be photographed, as well as in adjusting the direction of the X-rays.

Secured to the adapter 41 is a pin 49 which, when the adapter 41 is fitted onto the end face of the housing 22, throws a change-over switch 51 through an opening 50 in the end wall of the housing 22. The function of the switch 51 will be explained in more detail below with reference to FIG. 4.

The basic diagram, FIG. 4, shows the power supply for the X-ray tube 1 and the circuitry of all other parts accommodated in the compact unit enclosed by the cover 29 and the outer housing 22. Reference numbers 53 to 57 symbolically designate the individual slip rings 35. The mains voltage is supplied to the primary winding of a high-voltage transformer 62 via terminals 58 and 59, the slip rings 53 and 54, and a make contact 60 of a switching relay 61. As shown in FIG. 3, the casing 18 is divided by a partition 63 into two chambers 64 and 65. The transformer 62, which is situated in the chamber 64, has a first secondary winding 66 for feeding a filament 67 of the X-ray tube 1 and a second secondary winding 68 for producing the high voltage necessary for operating the X-ray tube 1. Disposed within the chamber 65 is a non-magnetic pipe piece 69 in which a socket 70 for the X-ray tube 1 is secured. Through the pipe piece 69 there extend two conductors 71 and 72 connecting the first secondary winding 66 and one terminal of the second secondary winding 68 to the filament 67 of the X-ray tube 1. The other terminal of the secondary winding 68 is connected via a terminal 73 and a conductor 74 to the beam current monitor 20 and, via the latter, grounded. Disposed within the pipe piece 69 is an induction coil 75 situated in the center of an excitation coil 75' encircling the casing 18. The induction coil 75 forms part of the bias source 12, which further comprises a rectifier 76 and a smoothing capacitor 77. The AC-voltage terminals of the rectifier 76 are connected to the induction coil 75, while the positive terminal of the rectifier 76 is connected to the conductor 71 and the negative terminal thereof to the modulator electrode 3 of the X-ray tube 1 by the conductor 11. The bias of the modulator electrode 3 can be changed by changing the energizing current flowing through the excitation coil 75' without the necessity of actuating or controlling any circuit means with the casing 18 for that purpose.

It is necessary to change the bias of the modulator electrode 3 because for operating the apparatus to obtain extra-oral photographs, a lower radiation intensity is used than when the apparatus is being employed for obtaining intra-oral photographs. The diameter of the focal spot is preferably between 0.05 and 1.5 mm. For the purpose of changing the radiation intensity, i.e., for changing the bias of the modulator electrode 3, the excitation coil 75' is connectible to a conductor 78, which is connected to the slip ring 54, on the one hand, and via two series-connected capacitors 79 and 80, via the change-over switch 51, and via one or the other of the slip rings 55 or 56 to one of the terminals 81 or 82, on the other hand, to which terminals a voltage is supplied by the control unit 13, depending upon the selected function. The capacitor 80 is by-passed through a break contact 83 of a switching relay 84 when this relay is not energized. When the capacitor 80 is short-circuited, a greater energizing current flows through the excitation coil 75' than when the two capacitors 78 and 80 are connected in series. In the latter case, a lower bias voltage is produced for the modulator electrode 3, causing the X-ray radiation intensity to be greater.

The beam current monitor 20 comprises a monitoring relay 85 and two series-connected shunts 86 and 87, one of which, the shunt 86, is a variable resistor connected in parallel with a make contact 88 of the switching relay 84. When the apparatus is in the operating state for making an extra-oral photograph, the beam current monitor 20 responds when the beam current is greater than 0.3–0.4 mA, i.e., the monitoring relay 85 attracts and closes a make contact 89 which is connected in series with a relay 90. The relay 90 comprises a self-holding contact 91 and a break contact 92. The self-holding contact 91 is connected in parallel with the make contact 89 of the monitoring relay 85, so that the relay 90 remains attracted when the monitoring relay 85 has been energized only briefly. The break contact 92 is situated in the circuit of the switching relay 61 of the circuit-breaking device 15. When the monitoring relay 85 responds, the relay 90 attracts and, owing to the self-holding contact 91, remains attracted, causing the switching relay 61 to drop out and the make contact 60 associated therewith to be opened. Owing to the opening of the make contact 60, the current supply to the high-voltage transformer 62 is interrupted, i.e., the apparatus is shut off.

When the apparatus is in the operating state for making an intra-oral photograph, the make contact 88 in the beam current monitor 20 is closed, and the variable resistor 86 is by-passed. In order for the monitoring relay 85 to respond, a beam current of about 3–4 mA is necessary in this state. After the monitoring relay 85 has responded, the relay 90 and the switching relay 61 operate as described above. Connected in parallel with the switching relay 61 is an indicator lamp 93 which lights up when the apparatus is ready for operation and goes out as soon as the monitoring relay 85 has responded.

The circuit-breaking device 15, the beam current monitor 20, and the function selector switching device 21, except for the change-over switch 51 actuatable by the adapter 41, are disposed on the annular printed wiring board 32 encircling the casing 18. The excitation coil 75' is secured to the printed wiring board 32 by means of three spacer bolts 94, only one of which is shown in FIG. 3.

FIG. 5 is a circuit diagram of the control unit 13 by means of which the entire apparatus can be controlled and operated. The control unit 13 is connected to the mains voltage and to protective ground over the preferably three-wire line 14 and terminals 95, 96, and 97. The phase voltage at the terminals 95 and 96 is supplied to an auto-transformer 100 via a differential current monitor 97, a fuse 98, and a voltage selector switch 99. The differential current monitor 97 disconnects the auto-transformer 100 from the terminals 95 and 96 when the current in the two connecting lines is not equally high, which may happen, for example, if one of these conductors has a ground leak. The protective ground is supplied to the devices in the housing 22 via an output terminal 101, a wire of the multiple line 16, a terminal 102 (FIG. 4), and the slip ring 57. An output terminal 103 of the control unit 13 is connected to the terminal 59 over another wire of the multiple line 16, and a terminal 104 is connected to the terminal 58 over still another wire of the multiple line 16. Output terminals 105 and 106 of the control unit 13 are connected to the terminals 81 and 82, respectively, over further wires of the multiple line 16.

Connected in between the terminal 101 for connecting the protective ground and the "high" output terminal of the auto-transformer 100 are a series-connected glow lamp 107 and resistor 108. The glow lamp 107, by-passed through a resistor 109, lights up when the protective ground is correctly connected and goes out when the protective ground is lacking. Furthermore, a series connection comprising a fuse 110, a diode 111, a protecting resistor 112, a photosensitive resistor 113, and a relay 114 is connected at the output of the auto-transformer 100. The photosensitive resistor 113 is disposed opposite the glow lamp 107 in such a way that it is illuminated by this glow lamp when the latter lights up. The protecting resistor 112 and the photosensitive resistor 113 are so selected that the relay 114 attracts when the glow lamp 107 lights up and drops out when the glow lamp 107 is not lit. The relay 114 comprises a single switching contact 115 which switches the voltage emanating from the auto-transformer 100 to a conductor 116 when the relay 114 attracts and to a further glow lamp 117 when the relay 114 drops out. A capacitor 118 is connected in parallel with the relay 114 for increasing the sensitivity of response. When the voltage emanating from the auto-transformer 100 is through-connected to the conductor 116, this is indicated by a voltmeter 119. When the relay 114 cannot attract owing to the lack of the protective ground, this is indicated by the glow lamp 117.

The control unit 13 comprises a manually-operated double-pole switch having a first switching contact 120 and a second switching contact 121. This switch serves for selecting the function of the apparatus. When the switch is in the position shown in FIG. 5, the apparatus is used for obtaining intra-oral photographs. The voltage on the conductor 116 is supplied to the switching relay 84 via the first switching contact 120, the output terminal 106, the terminal 82, and the slip ring 55, whereby the break contact 83 is opened and the make contact 88 is closed. The output terminal 105, the terminal 81 connected thereto, and the slip ring 56 are currentless in the position of the switching contact 120 shown in FIG. 5. When the change-over switch 51 is in the position illustrated in FIG. 4, i.e., when the adapter 41 is not fitted on the end face of the housing 22, no voltage is supplied to the relay 90 and the switching relay 61, and the apparatus cannot be started up because the positions of the switch 51 actuatable by the adapter 41 and the manually-operated switch on the control unit 13 do not agree. Not until the adapter 41 is fitted onto the housing 22 is the change-over switch 51 thrown into the non-shown position, whereupon the relay 90 and the switching relay 61 attract. Only then is the apparatus ready for making an intra-oral photograph.

Through operation of a double-pole push button 122 on the control unit 13, the voltage on the conductor 116 reaches both a time-lag relay 123 and the second switching contact 121 of the manually-operated switch. The time-lag relay 123 comprises two make contacts 124 and 125. Via the make contact 124, a relay 126 having a single make contact 127 is energized. The make contact 125 of the time-lag relay 123 and the make contact 127 of the relay 126 are connected in common to the second switching contact 121. Upon operation of the push button 122, first the time-lag relay 123 attracts and switches the voltage on the conductor 116, with the aid of the make contact 125, via a series resistor 128 to the output terminal 104, which is in turn connected to the primary winding of the high-voltage transformer 62 via the terminal 58, the slip ring 53, and the closed make contact 60 of the switching relay 61. Not until a few milliseconds after attraction of the time-lag relay 123 is the relay 126 energized via the make contact 124 of the time-lag relay 123, and the make contact 127 of the relay 126 by-passes the series resistor 128 so that thereafter the full voltage is operative at the high-voltage transformer 62. The series resistor 128 prevents the occurrence of too high voltage peaks when the high-voltage transformer 62 is turned on.

After a period of time adjustable by means of a variable resistor 129, the time-lag relay 123 drops out again, whereby the make contacts 125 and 127 are opened, and the relay 126 likewise drops out. This causes the make contact 127 to open and the voltage on the conductor 116 to be cut off from the high-voltage transformer 62. The adjustable drop-out time of the time-lag relay 123 is identical with the exposure time for the photographs. During the time when there is voltage at the output terminal 104, i.e., at the high-voltage transformer 62, a glow lamp 130 lights up and thereby indicates the exposure time, which is adjustable between 0.5–1.5 seconds, for instance.

If an extra-oral photograph is to be made, the adapter 41 is removed from the housing 22, whereby the change-over switch 51 returns to the position shown in FIG. 4. At the control unit 13, the manually-operated switch having the two switching contacts 120 and 121 is thrown into the position not shown in FIG. 5. The voltage on the conductor 116 is conducted via the first switching contact 120, the output terminal 105, the terminal 81, the slip ring 56, and the change-over switch 51 into the function selector switching device 21, thence via the closed break contact 83 of the dropped-out switching relay 84 and the capacitor 79 to the excitation coil 75', and furthermore via the closed break contact 92 of the non-energized relay 90 to the switching relay 61, which closes its make contact 60. The drop-out of the switching relay 84 causes, firstly, the by-passing of the capacitor 80 through the break contact 83, whereby the bias of the modulator electrode 3 becomes greater, and secondly, the insertion of the variable resistor 86, whereby the beam current monitor 20 becomes more sensitive.

The increase in the bias voltage of the modulator electrode 3 causes the beam current to become smaller and thus the X-ray intensity produced to become lower.

If, thereafter, the push button 122 is operated, the voltage on the conductor 116 is supplied to the time-lag relay 123 as already described above, and the latter controls the relay 126. However, a voltage reduced by about 20 volts is supplied to the switching contact 121 via another conductor 131 and the second contact of the push button 122, so that a voltage reduced by the said amount reaches the high-voltage transformer 62 via the make contact 125 and the series resistor 128 or via the make contact 127.

A reduced voltage is supplied to the high-voltage transformer 62 in the operating state for making extra-oral photographs because the beam current is less then for making intra-oral photographs, and hence the transformer 62 is less heavily loaded. If the voltage applied to the transformer 62 were not reduced, the high voltage produced would be too high. The voltage supplied to the transformer 62 is preferably reduced to the extent that the voltage produced by the transformer 62 is identical during both possible functions. The positions of the two switching contacts 120 and 121 of the manually-operated switch in the control unit 13 are optically indicated by indicator lamps 132 and 133.

Since no test electrodes are necessary in the region of the anticathode 5 for precisely directing the cathode-ray onto the tip of the anticathode, the diameters of the anode tube 52 and, consequently, of the protective sleeve 40 can be kept much smaller than is possible in the case of known apparatus. This means that the patient's mouth need not be opened so far for extra-oral photographs.

For obtaining extra-oral photographs, the end of the protective sleeve 40 is inserted between two molars 134 and 135 of the person to be examined, whose head is partially and diagrammatically depicted in FIG. 6. The target surface 6 of the anticathode 5 is then preferably situated between the two second molars of the one half of the upper and lower jaws, and the protective sleeve 40 is held in place by slight biting pressure of the molars 134 and 135. FIG. 7 shows the position of the protective sleeve 40 with respect to the lower jaw. The target surface 6 of the anticathode 5 is situated perpendicular to the plane of the drawing and is preferably inclined at an angle of 45° with respect to the cathode-ray axis, so that the cone of X-rays exiting through the X-ray-permeable protective sleeve 40, as indicated by dashed lines 136, irradiates the opposite halves of the upper and lower jaws. A film (not shown) is disposed outside the irradiated jaw-halves and accordingly exposed.

The advantage of this extra-oral photographing technique as compared with that of the prior art, in which the X-ray source is disposed in the middle of the arch of teeth, is that the image quality is improved through the substantially doubled distance between the objects being photographed and the X-ray source. The latter can easily be positioned in the most favorable location and held firmly in this position by a light biting pressure.

The cone of X-rays exiting from the protective sleeve 40 is preferably limited by a "window" therein (not shown) so that the molars resting directly against the protective sleeve are not exposed to any increased radiation effect.

What is claimed is:

1. In apparatus for obtaining extra- and/or intra-oral dental X-ray photographs, of the type wherein high-voltage transformer and part of an X-ray tube are disposed in an inner casing contained within an outer housing, from an end face of which there projects an anode tube of said X-ray tube containing an anticathode and surrounded by an X-ray-permeable protective sleeve, the improvement comprising:
    a plane anticathode target surface disposed within said anode tube and inclined with respect to the cathode-ray axis of said X-ray tube,
    regulating means dependent upon the operating state of said apparatus for varying the cathode-ray current and/or the size of the focal spot,
    an adapter designed to be fitted over said protective sleeve and secured to said end face of said outer housing for obtaining said intra-oral X-ray photographs,
    a change-over switch disposed within said outer housing near said end face thereof and actuatable by said adapter for influencing said regulating means, and
    an X-ray-proof jacket forming part of said adapter and designed to fit over said protective sleeve coaxially therewith.

2. Apparatus in accordance with claim 1, wherein an aperture is provided in said X-ray-proof jacket, said aperture being situated in the vicinity of said anticathode when said adapter is fitted over said sleeve, said adapter further comprising an angled-off portion, extending at right angles to said jacket and parallel to the axis of passage of said aperture, and a tapered cover for closing off said angled-off portion.

3. Apparatus in accordance with claim 1, wherein said X-ray tube further comprises a modulator electrode and said regulating means comprise an induction coil, disposed within said inner casing between said transformer and the end of said X-ray tube remote from said anticathode, and an excitation coil disposed outside said casing and encircling said induction coil, a rectifier and a smoothing capacitor being connected to said induction coil for producing a bias voltage for said modulator electrode, an alternating-current resistor being connected in series with said excitation coil for varying the energizing current, and a circuit element being provided for by-passing said alternating-current resistor.

4. Apparatus in accordance with claim 3, wherein said transformer includes a secondary winding having at least two terminals, said apparatus further comprising a control unit having a function selector switch, a switching relay responsive to said function selector switch and having a break contact, a beam current monitor for producing a disconnection signal when said cathode-ray current exceeds a predetermined value, said beam current monitor being connected in between one of said terminals and ground, and means for varying the sensitivity of said beam current monitor as a function of the position of said change-over switch.

5. Apparatus in accordance with claim 4, wherein said outer housing is axially symmetrical with respect to the longitudinal axis of said X-ray tube, said apparatus further comprising a fastening ring disposed adjacent to said outer housing, a protective cover disposed adjacent to said fastening ring at the end of said apparatus remote from said anticathode, said inner casing surrounding said transformer, said induction coil, and part of said X-ray tube remote from said anticathode being enclosed within said outer housing, said fastening ring, and said protective cover and said casing and said housing being mounted for rotation about their longitudinal axes in said fastening ring, an annular printed wiring board encircling said inner casing, said regulating means, said switching relay, and said beam current monitor being disposed upon said annular printed wiring board, and a plurality of slip rings disposed within said fastening ring and encircling said inner casing for supplying mains voltage for said transformer, current for said excitation coil, and a control voltage for said switching relay.

6. Apparatus in accordance with claim 5, further comprising a further switching relay disposed on said printed wiring board and connected to said change-over switch, a make contact forming part of said further switching relay and disposed in a primary circuit of said transformer, and two control lines connecting said change-over switch and said function selector switch in said control unit in such a way that said further switching relay is energized only when said adapter is removed from said protective sleeve for obtaining an extra-oral photograph and said function selector switch is positioned for extra-oral photographs or when said adapter is fitted on said protective sleeve for obtaining an intra-oral photograph and said function selector switch is positioned for intra-oral photographs.

* * * * *